(12) United States Patent
Keelen

(10) Patent No.: US 12,396,879 B2
(45) Date of Patent: Aug. 26, 2025

(54) AUTOMATED CATHETER AND CHEST TUBE DEVICES AND RELATED SYSTEMS

(71) Applicant: Tessefi Innovations, Inc., Rocky Mount, NC (US)

(72) Inventor: Mengesha Keelen, Rocky Mount, NC (US)

(73) Assignee: Tessefi Innovations, Inc., Rocky Mount, NC (US)

( * ) Notice: Subject to any disclaimer, the term of this patent is extended or adjusted under 35 U.S.C. 154(b) by 532 days.

(21) Appl. No.: 17/618,092

(22) PCT Filed: Jun. 8, 2020

(86) PCT No.: PCT/US2020/036640
§ 371 (c)(1),
(2) Date: Dec. 10, 2021

(87) PCT Pub. No.: WO2020/241893
PCT Pub. Date: Dec. 17, 2020

(65) Prior Publication Data
US 2022/0296406 A1    Sep. 22, 2022

Related U.S. Application Data

(60) Provisional application No. 62/861,165, filed on Jun. 13, 2019, provisional application No. 62/861,169, filed on Jun. 13, 2019.

(51) Int. Cl.
*A61F 5/44*    (2006.01)
*A61B 5/00*    (2006.01)
(Continued)

(52) U.S. Cl.
CPC .............. *A61F 5/44* (2013.01); *A61B 5/1032* (2013.01); *A61B 5/208* (2013.01); *A61B 5/4875* (2013.01);
(Continued)

(58) Field of Classification Search
CPC ......... A61F 5/44; A61B 5/1032; A61B 5/208; A61B 5/4875; A61B 5/6852; A61B 5/026;
(Continued)

(56) References Cited

U.S. PATENT DOCUMENTS 4,589,280 A * 5/1986 Carter .................... A61B 5/208
600/573
4,620,846 A * 11/1986 Goldberg .............. A61M 1/285
604/28
(Continued)

FOREIGN PATENT DOCUMENTS

CN    104981203 A    10/2015
CN    107736901 A    2/2018
(Continued)

OTHER PUBLICATIONS

European Search Report for Application No. 20823537 dated Jul. 19, 2022.
(Continued)

*Primary Examiner* — Nicholas J. Weiss
*Assistant Examiner* — Brandon W. Levy
(74) *Attorney, Agent, or Firm* — KDW FIRM PLLC

(57) ABSTRACT

Automated catheter and automated chest tube systems and devices. In some embodiments, the automated, or smart, catheter and chest tube of the present disclosure includes a housing for containing one or more collection reservoirs for collecting fluid, a flexible tube used to drain the fluid from either the bladder, chest cavity, or other appropriate bodily region, and a measuring device to measure the amount of fluid flowing through the flexible tube and into the collection reservoir(s). In some embodiments, the smart catheter and chest tube of the present disclosure includes one or more processors, one or more transmitters, and one or more
(Continued)

receivers to transmit and receive data regarding the volume and other characteristics of the fluid collected in the reservoirs and to receive commands for performing various functions. The alarms are triggered when certain predetermined liquid volume thresholds are exceeded or not exceeded.

19 Claims, 12 Drawing Sheets

(51) Int. Cl.
    *A61B 5/103*     (2006.01)
    *A61B 5/20*     (2006.01)
    *A61M 25/00*     (2006.01)
    *A61M 25/10*     (2013.01)

(52) U.S. Cl.
    CPC ....... *A61B 5/6852* (2013.01); *A61M 25/0017* (2013.01); *A61M 25/10* (2013.01)

(58) Field of Classification Search
    CPC ... A61B 5/0084; A61B 5/6853; A61B 5/1459; A61B 10/007; A61B 2562/0247; A61B 2562/0214; A61B 2562/228; A61B 5/6882; A61B 5/14539; A61B 5/14507; A61B 5/20; A61B 5/1473; A61B 5/201; A61M 25/0017; A61M 25/10; A61M 27/00; A61M 1/74; A61M 2210/1085; A61M 2205/18; A61M 2205/3334; A61M 5/1723
    See application file for complete search history.

(56) References Cited

U.S. PATENT DOCUMENTS

| | | | | |
|---|---|---|---|---|
| 4,745,929 | A * | 5/1988 | Silver | A61B 5/208 604/323 |
| 6,029,076 | A * | 2/2000 | Fiddian-Greene | A61B 5/036 600/353 |
| 7,264,616 | B2 | 9/2007 | Shehada et al. | |
| 7,722,584 | B2 * | 5/2010 | Tanaka | A61M 1/782 604/326 |
| 2005/0256447 | A1 * | 11/2005 | Richardson | A61M 25/0017 604/65 |
| 2009/0018424 | A1 * | 1/2009 | Kamath | A61B 5/14546 600/347 |
| 2013/0165877 | A1 | 6/2013 | Leeson et al. | |
| 2013/0318701 | A1 | 12/2013 | Stapleton et al. | |
| 2016/0051176 | A1 | 2/2016 | Ramos et al. | |
| 2016/0310711 | A1 | 10/2016 | Luxon et al. | |
| 2017/0020724 | A1 * | 1/2017 | Burnett | A61F 7/0085 |
| 2017/0113000 | A1 * | 4/2017 | Tobescu | A61M 25/0017 |
| 2017/0136209 | A1 | 5/2017 | Burnett et al. | |
| 2018/0214297 | A1 * | 8/2018 | Hughett | A61B 5/7445 |
| 2019/0069831 | A1 | 3/2019 | Kuck et al. | |

FOREIGN PATENT DOCUMENTS

| | | | |
|---|---|---|---|
| JP | 2012529649 A | 11/2012 | |
| JP | 2018533404 A | 11/2018 | |
| KR | 20030069757 A | 8/2003 | |
| WO | 2010144036 A1 | 12/2010 | |
| WO | WO-2016118943 A2 * | 7/2016 | ............... A61B 5/00 |
| WO | 2017070117 A1 | 4/2017 | |
| WO | 2018180229 A1 | 10/2018 | |
| WO | WO-2020/251893 A1 | 12/2020 | |

OTHER PUBLICATIONS

International Search Report and Written Opinion corresponding to International Patent Application No. PCT/US2020/036640 dated Sep. 4, 2020.

Japanese Office Action in JP Application No. 2021-573720, dated Dec. 3, 2024, 15 pages.

Second Chinese Office Action in CN Application No. 202080042815, dated Mar. 3, 2025, 13 pages.

* cited by examiner

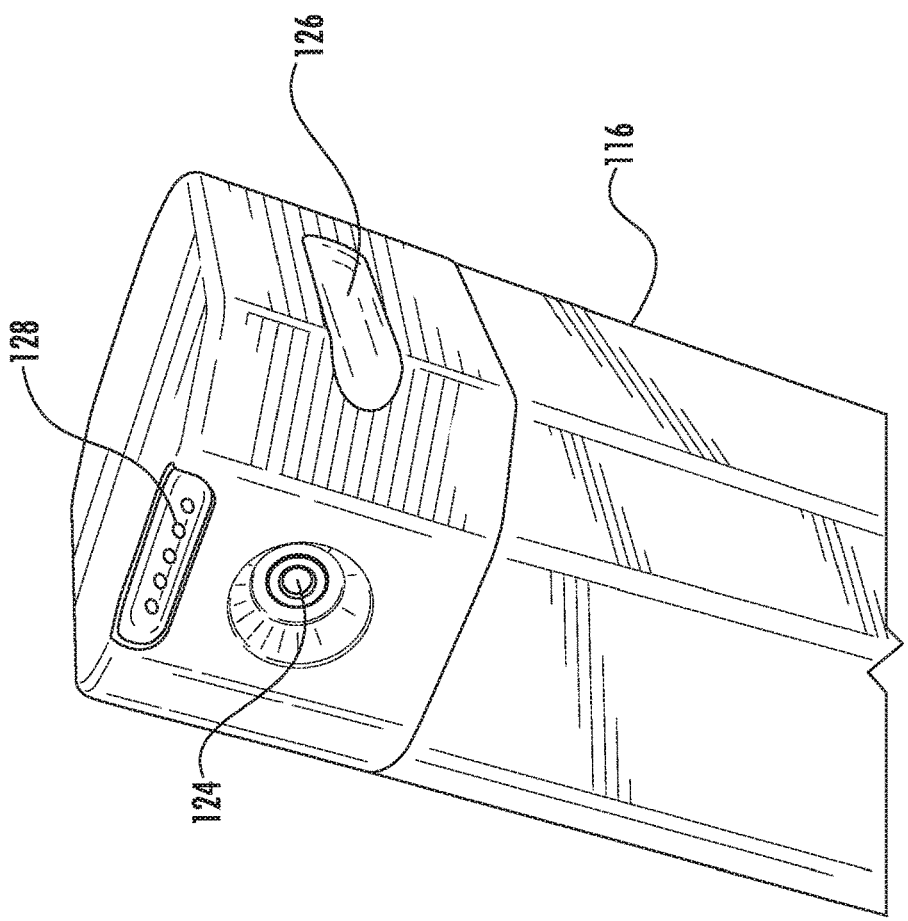
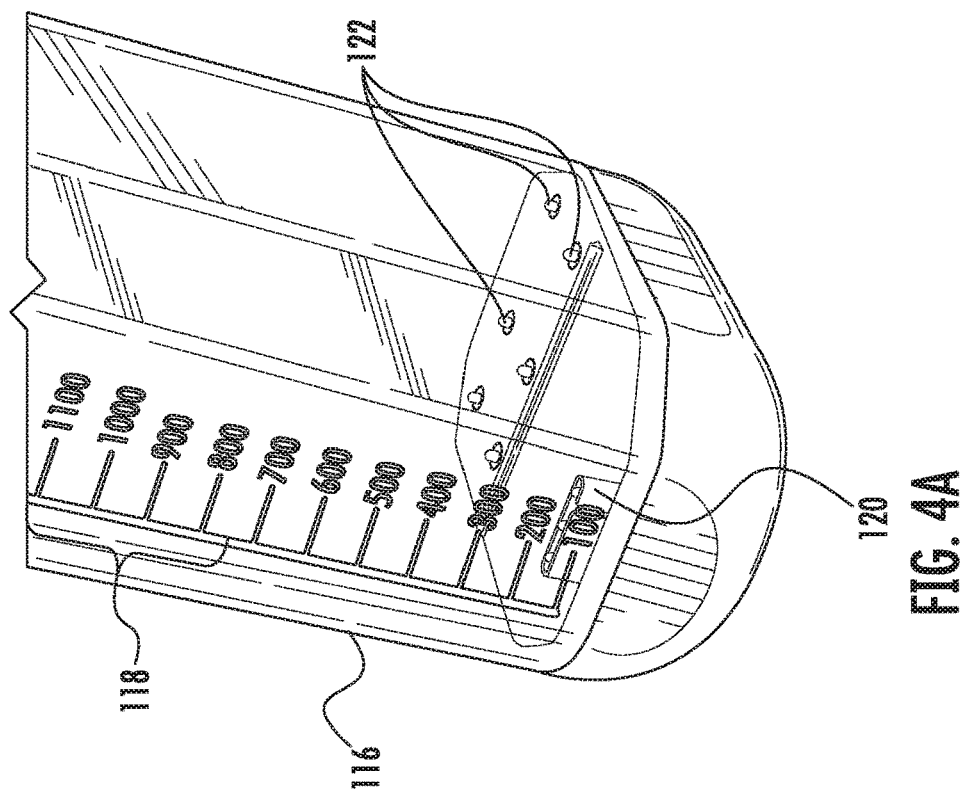
FIG. 4A
FIG. 4B

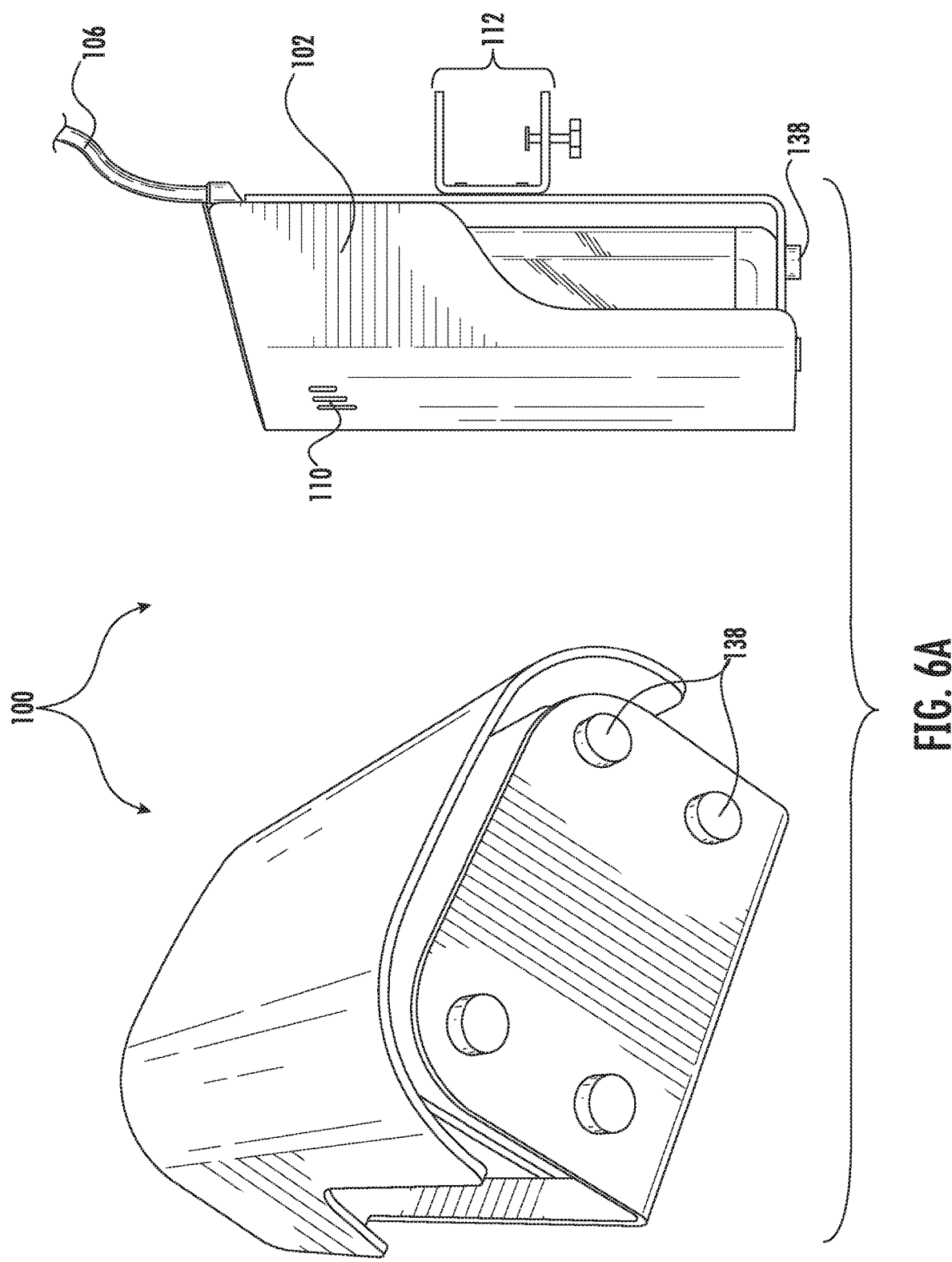

AUTOMATED CATHETER AND CHEST TUBE DEVICES AND RELATED SYSTEMS

CROSS-REFERENCE TO RELATED APPLICATIONS

This application is a national phase application of PCT International Patent Application PCT/US2020/036640, filed Jun. 8, 2020, which claims priority to U.S. Provisional Patent Application Ser. No. 62/861,169, filed Jun. 13, 2019, and U.S. Provisional Patent Application Ser. No. 63/861,165, filed Jun. 13, 2019, the entire disclosures of which are incorporated by reference herein.

TECHNICAL FIELD

The subject matter herein generally relates to the field of catheters, chest tubes, and related devices. The subject matter herein more particularly relates to, automated catheter devices and related systems, including urinary catheters and chest tubes.

BACKGROUND

Modern medical catheters, particularly Foley catheters, are used to collect urine in patients while admitted to hospitals and medical facilities. However, the amount of urine collected by the catheter is not automatically calculated, and the data is not available electronically via a computer. Instead, urine output must be manually measured or observed, and the data manually charted or recorded when time permits. This can be detrimental to the patient because if a nurse, Nursing Assistant, technician or other medical professional forgets to chart the amount of periodic output a provider will assume there was no urine output. There are numerous potentials for errors including, but not limited to spilled urine and incorrect or imprecise measurements. This is crucial in providing proper medical care. For example, if a patient is admitted with a diagnosis such as diabetes insipidus, proper recording and utilization of urine output can be a life or death proposition.

In a similar vein, chest tubes are used to collect air, fluid, pleural effusion, blood, chyle, or pus from the intrathoracic space of a patient while admitted to hospitals and medical facilities, and/or otherwise under medical care. However, the amount of air, fluid, pleural effusion, blood, chyle, or pus collected by the chest tube is not automatically calculated, and the data is not available electronically via a computer. Instead, the amount of air or fluid output must be manually measured or observed, and the data manually charted or recorded when time permits. Similarly to the urine catheter issues described above, if the nurse, or other professional, fails to chart the periodic air, fluid, pleural effusion, blood, chyle, or pus collected from the patient, a provider will assume there was no output. These types of charting are critical for receiving the proper treatment and, just like with the catheter, the potential consequence for error could be deadly. For example, if a patient is admitted with a particular condition, proper recording and utilization of air, fluid, pleural effusion, blood, chyle, or pus output can be a life or death proposition.

Thus, what is needed is an automated system delivering results in real-time or a device that collects, measures and/or records urine output and/or air, fluid, pleural effusion, blood, chyle, and/or puss output with minimal or no effort by medical personnel. Such need is addressed by the devices and system described herein.

SUMMARY

In accordance with this disclosure, smart catheter and smart chest tube devices and systems are provided. In one aspect, a smart catheter is provided, the smart catheter comprising: a flexible tube with an opening at a first end; a drainage port at an opposing second end; an inflatable balloon at the first end, and proximate to the opening; a balloon port at the second end and proximate to the drainage port; and a measuring device, comprising one or more sensors, integrated into or attached to the flexible tube and configured to measure an amount of fluid flowing therethrough. In some embodiments, the smart catheter is configured to drain urine from a bladder of a patient, and the measuring device is a flow meter sensor. In some embodiments, the drainage port is configured to connect or otherwise attach to one or more collection reservoirs; and the smart catheter is configured to deposit urine in the one or more collection reservoirs.

In some further embodiments, the flow meter sensor is configured to measure the amount of urine deposited into the one or more collection reservoirs. In some embodiments, the flexible tube comprises two separated channels or lumens running along a length of the flexible tube, wherein a first lumen, open at both ends, connects the opening at the first end to the drainage port at the second end, wherein the second lumen connects the inflatable balloon to the balloon port. In some embodiments, the measuring device is integrated into and/or along a length of the flexible tube at any suitable location. In some embodiments, the measuring device comprises a transmitter that is configured to transmit data to one or more processors in communication with the measuring device.

In some further embodiments, the transmitted data comprises urine flow data; the one or more processors is configured to store and monitor the urine flow data; the one or more processors is configured to monitor an amount of urine deposited into one or more collection reservoirs of the smart catheter; and the one or more processors is configured to transmit a warning signal or trigger an alarm when at least one of the one or more collection reservoirs of the smart catheter reaches one or more thresholds. In some embodiments, the one or more processors is configured to transmit a warning signal or trigger an alarm when there is a malfunction of the smart catheter. In some embodiments, components of the smart catheter are housed in an enclosure comprising a display screen; and the display screen is configured to display fill levels of one or more collection reservoirs of the smart catheter.

In some embodiments, the enclosure further comprises a transparent or non-transparent door; and wherein each of the one or more collection reservoirs is either transparent or non-transparent. In some embodiments, one or more of the collection reservoirs comprises a total dissolved solids meter and/or a color sensor configured to detect and measure a color or shade of a fluid. In some embodiments, one or more of the collection reservoirs comprises a quick connect port to connect the one or more collection reservoirs to the smart catheter. In some embodiments, when a first collection reservoir is removed from the smart catheter, the smart catheter is configured to automatically select a second collection reservoir and start draining urine into the second collection reservoir. In some embodiments, each of the one or more collection reservoirs comprises an electrical connection configured to provide power to various components in a respective collection reservoir and to connect the one or more processors to the various components in the respective collection reservoir.

In another aspect, a smart catheter system is provided, the smart catheter system comprising a smart catheter of any of the above embodiments; and an external device, wherein the external device comprises a tablet, computer, phone, smart watch, audio device or display device. In some embodiments, wherein the system further comprises: a power source, one or more processors, memory, a receiver or transmitter, a display, an accelerometer, a speaker and/or a tactile signal device, wherein the smart catheter, power source, one or more processors, memory, receiver or transmitter, display, accelerometer, speaker or tactile signal device are interconnected with one another. In some embodiments, the display is configured to display information about the patient and/or the smart catheter.

In some embodiments, the display is configured to display identification information about the patient as well as information regarding the patient's urine; and wherein the display is configured to display information about a capacity of each of the one or more collection reservoirs or a warning or error message. In some embodiments, the smart catheter system comprises a computer program product comprising computer executable instructions embodied in a computer readable medium for performing steps comprising receiving an electrical signal from a measuring apparatus, processing the electrical signal to calculate data pertaining to a measured volume, and relaying the data to the electronic display, speaker, tactile signal device or external device. In some embodiments, the smart catheter system are configured to measure and calculate a volume of urine or other body fluid produced by a patient every 30 minutes or Q one hour, wherein the calculated volume is processed by a computer and entered into an electronic charting system.

In some embodiments, the smart catheter system is configured to measure and calculate the volume of urine or other body fluid produced by a patient and activate an alarm if the volume of urine and/or other body fluid is above and/or below a predetermined threshold. In some embodiments, the smart catheter or smart catheter system of any of the above embodiments, where the smart catheter or smart catheter system is configured as a chest tube.

In another aspect a smart chest tube is provided, the smart chest tube comprising: a flexible tube with an opening at a first end; a drainage port at the opposing second end; and a measuring device, comprising one or more sensors, integrated into or attached to the flexible tube and configured to measure an amount of fluid flowing therethrough. In some embodiments, the chest tube is configured to drain air, fluid, pleural effusion, blood, chyle, or pus from a chest cavity of a patient, and wherein the measuring device is a fluid flow meter sensor. In some embodiments, the drainage port is configured to connect or otherwise attach to one or more collection reservoirs; and the smart chest tube is configured to deposit air, fluid, pleural effusion, blood, chyle, or pus in the one or more collection reservoirs. In some embodiments, the flow meter sensor is configured to measure the amount of air, fluid, pleural effusion, blood, chyle, or pus deposited into the one or more collection reservoirs.

In some further embodiments, the measuring device is integrated into and/or along a length of the flexible tube at any suitable location. In some embodiments, the measuring device comprises a transmitter that is configured to transmit data to one or more processors in communication with the measuring device. In some embodiments, the transmitted data comprises flow data regarding air, fluid, pleural effusion, blood, chyle, or pus flowing through the flexible tube and measured by the measuring device; the one or more processors is configured to store and monitor the flow data; the one or more processors is configured to monitor an amount of air, fluid, pleural effusion, blood, chyle, or pus deposited into one or more collection reservoirs of the smart chest tube; the one or more processors is configured to transmit a warning signal or trigger an alarm when at least one of the one or more collection reservoirs of the smart chest tube reaches one or more thresholds.

In some further embodiments, the one or more processors is configured to transmit a warning signal or trigger an alarm when there is a malfunction of the smart chest tube. In some embodiments, components of the smart chest tube are housed in an enclosure comprising a display screen; and the display screen is configured to display fill levels of one or more collection reservoirs of the smart chest tube. In some embodiments, the chest tube system is configured to measure and calculate a volume of air or a body fluid produced by a patient and activate an alarm if the volume of air or a body fluid is above or below one or more predetermined thresholds.

In some further embodiments, one or more of the collection reservoirs comprises a total dissolved solids meter and/or a color sensor configured to detect and measure a color or shade of a fluid. In some embodiments, one or more of the collection reservoirs comprises a quick connect port to connect the one or more collection reservoirs to the smart chest tube. In some embodiments, when a first collection reservoir is removed from the smart chest tube, the smart chest tube is configured to automatically select a second collection reservoir and start draining body fluid into the second collection reservoir. In some embodiments, each of the one or more collection reservoirs comprises an electrical connection configured to provide power to various components in a respective collection reservoir and to connect the one or more processors to the various components in the respective collection reservoir.

In some embodiments, a smart chest tube system is provided, the system comprising a smart chest tube of any of the above claims; and an external device, wherein the external device comprises a tablet, computer, phone, smart watch, audio device or display device. In some embodiments, the system further comprises: a power source, one or more processors, memory, a receiver or transmitter, a display, an accelerometer, a speaker and/or a tactile signal device, wherein the power source, one or more processors, memory, receiver or transmitter, display, accelerometer, speaker or tactile signal device are interconnected with one another. In some embodiments, the display is configured to display information about the patient and/or the smart catheter.

In some embodiments, the display is configured to display identification information about the patient as well as information regarding the patient's urine; and wherein the display is configured to display information about a capacity of each of the one or more collection reservoirs or a warning or error message. In some embodiments, the smart chest tube system further comprises a computer program product comprising computer executable instructions embodied in a computer readable medium for performing steps comprising receiving an electrical signal from a measuring apparatus, processing the electrical signal to calculate data pertaining to a measured volume, and relaying the data to the electronic display, speaker, tactile signal device or external device. In some embodiments, the smart chest tube system is configured to measure and calculate a volume of air or a body fluid produced by a patient every 30 minutes or Q one hour, wherein the calculated volume is processed by a computer and entered into an electronic charting system. In some further embodiments, the chest tube system is configured to measure and calculate the volume of air or a body fluid produced by a patient and activate an alarm if the volume of air or a body fluid is above and/or below a predetermined threshold.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which:

FIG. 4A and FIG. 4B are close-up views of vials or collection reservoirs of a smart catheter device according to an embodiment of the presently disclosed subject matter;

FIG. 6A is a perspective bottom view and a side view of a smart catheter device according to an embodiment of the presently disclosed subject matter;

DETAILED DESCRIPTION

Figure 1A:
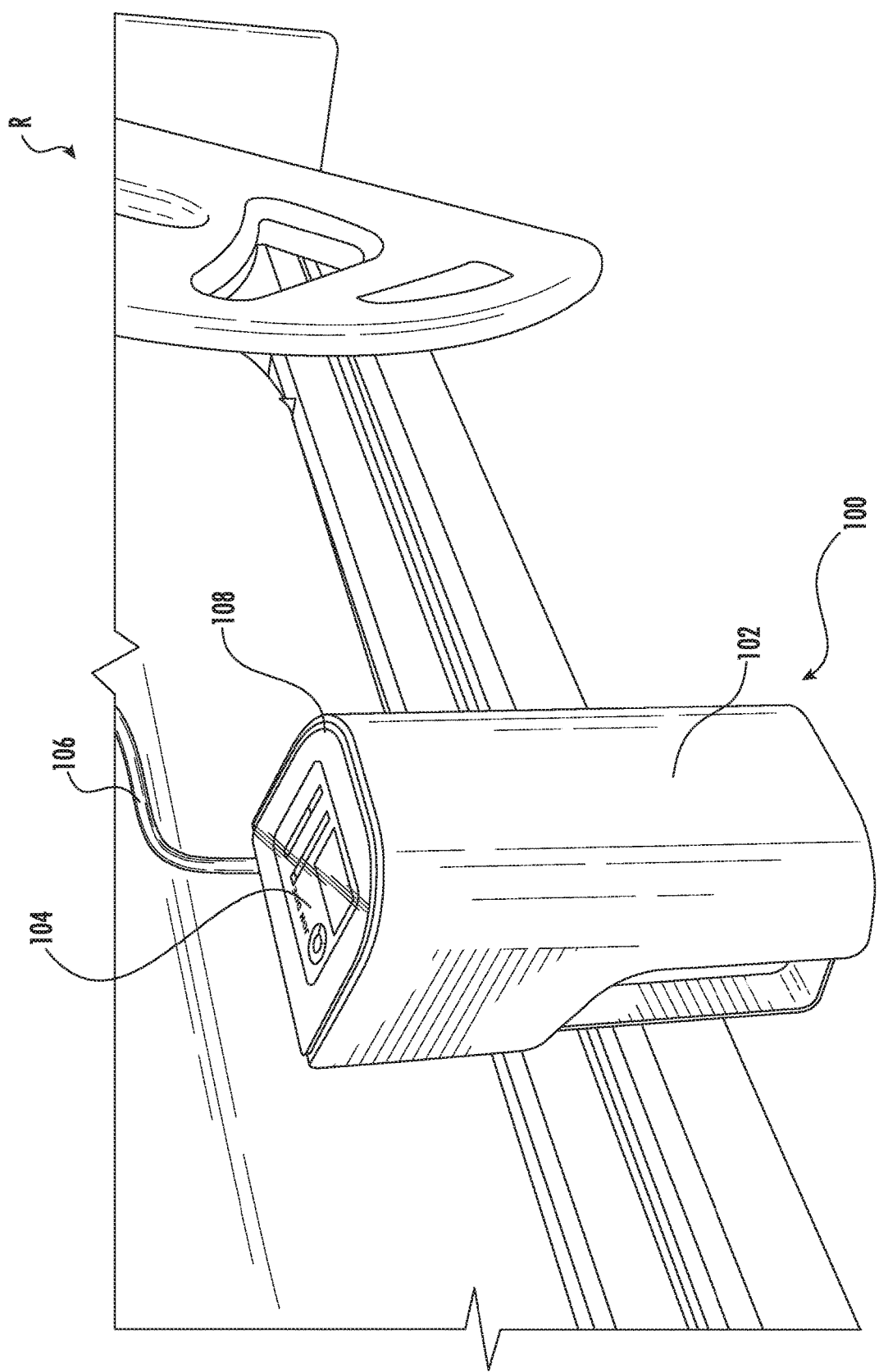
FIG. 1A is a perspective view of a smart catheter device according to an embodiment of the presently disclosed subject matter.

The present subject matter provides automated or smart catheter systems and devices and automated or smart chest tube systems and devices. In one aspect, the present subject matter provides smart catheter systems and devices for draining, storing, and measuring urine from a patient and warning or alerting healthcare officials once the urine levels get to a certain level or the device malfunctions. In similar aspect, the present subject matter provides smart chest tube systems and device for draining, storing, and measuring bodily fluids from a patient and warning or alerting healthcare officials once the bodily fluid levels reach a certain threshold. While the following terms are believed to be well understood by one having ordinary skill in the art, the following definitions are set forth to facilitate explanation of the presently disclosed subject matter.

Unless defined otherwise, all technical and scientific terms used herein have the same meaning as commonly understood to one having ordinary skill in the art to which the presently disclosed subject matter belongs. Although, any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in this application, including the claims. Thus, for example, reference to "a vial" can include a plurality of such vials, and so forth.

Unless otherwise indicated, all numbers expressing quantities of length, diameter, width, and so forth used in the specification and claims are to be understood as being modified in all instances by the terms "about" or "approximately". Accordingly, unless indicated to the contrary, the numerical parameters set forth in this specification and attached claims are approximations that can vary depending upon the desired properties sought to be obtained by the presently disclosed subject matter.

As used herein, the terms "about" and "approximately," when referring to a value or to a length, width, diameter, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate for the disclosed apparatuses and devices.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and sub-combinations of A, B, C, and D.

Smart Catheter Devices and Systems

Urinary catheters are used to collect urine in patients while admitted to hospitals and medical facilities, as well as at home and for chronic use. The urine output is manually collected and measured by nurses and other medical professionals. Unfortunately, there is no automated system for performing this important task. Instead, urine output must be manually measured or observed, and the data manually charted or recorded, usually hours after. This is a crucial step in providing proper medical care, but due to the manual nature of this task it can easily be overlooked or delayed. An automated or smart system or device that collects, measures and/or records urine output with minimal or no effort by medical personnel would improve efficiency, accuracy, best practice, health care effectiveness and successful patient outcomes. The disclosed devices and systems fill this unmet need. Particularly, the disclosed devices and systems automatically collect, measure, calculate and record urine output and other related data. In some embodiments, such catheters and catheter systems can be referred to as a precise catheter, smart catheter, electronic catheter, and the like, or precise Foley, smart Foley, electronic Foley, and the like.

Figure 1B:
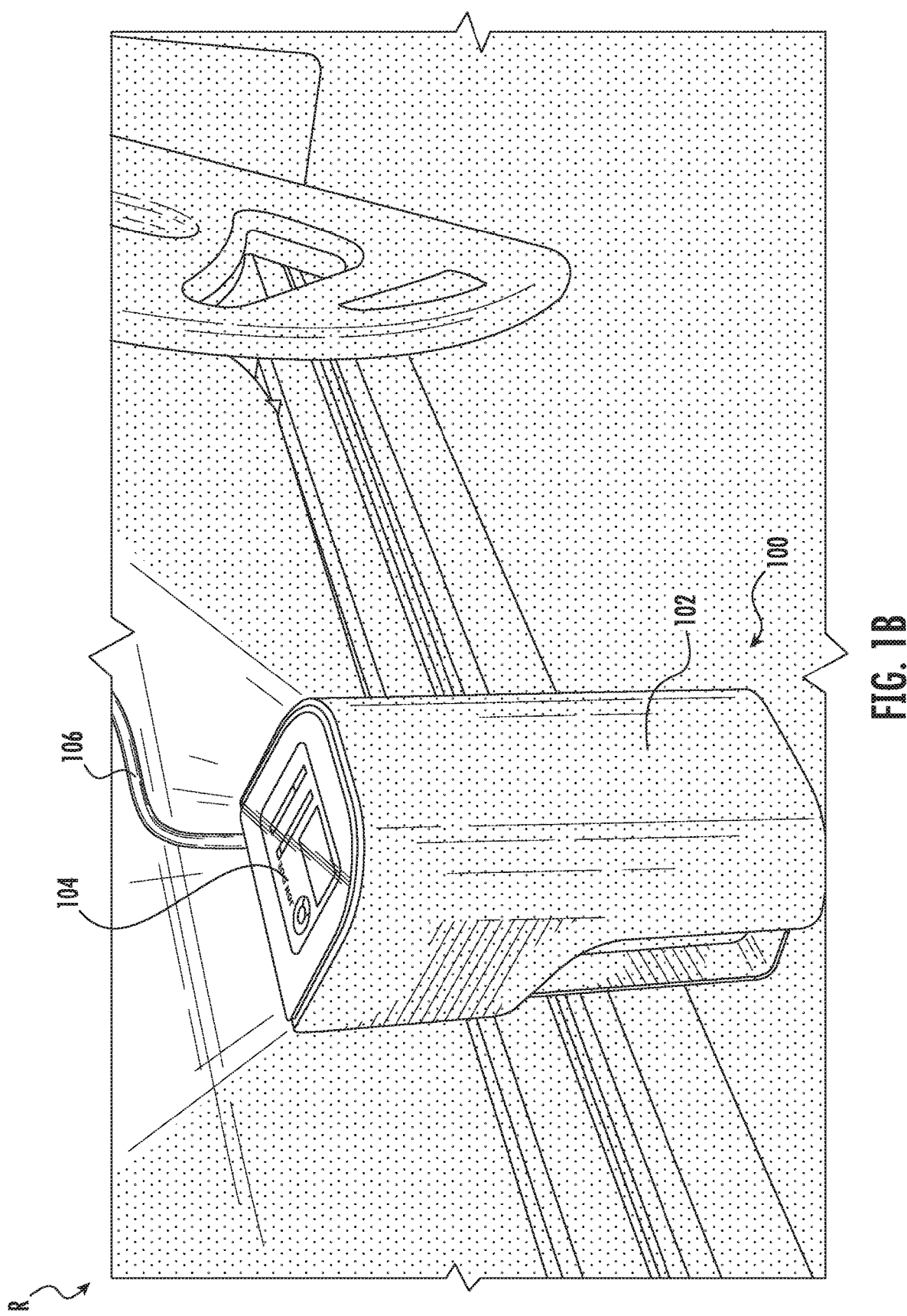
FIG. 1B is a perspective view of a smart catheter device according to an embodiment of the presently disclosed subject matter with a display glowing in the dark.

Referring to FIG. 1A, which depicts a perspective view of one embodiment of a possible smart catheter 100 of the present disclosure attached to the side of a hospital bed. In some embodiments, the smart catheter 100 can have an enclosure or housing that houses a subset of its components. The housing or enclosure can have a door 102 that swings open revealing any components within. In some embodiments, the smart catheter 100 can also comprise a display 104, a flexible tube 106 (i.e., the actual urinary catheter component), and a lighting element 108. Referring to FIG. 1B, in some embodiments, the lighting element 108 can light up the room it is in like a night light, allowing nurses, doctors, and other health professionals to view the display without disturbing the patient by cutting on the lights in the room to see the contents of the catheter collection reservoir(s). The characteristics of the various components are described further hereinbelow.

Figure 2B:
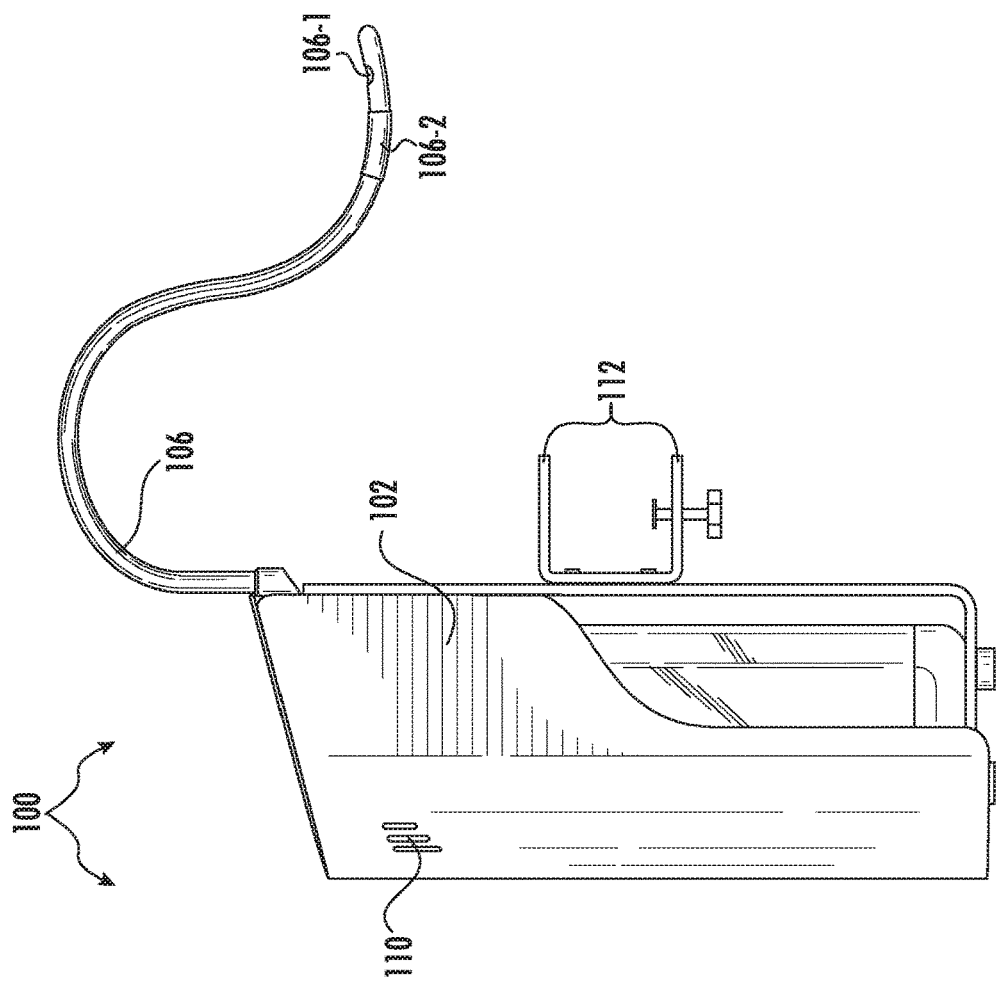
FIG. 2B and FIG. 2C depict a side view of a smart catheter device and illustrates the details of the flexible tube according to an embodiment of the presently disclosed subject matter.
Figure 2A:
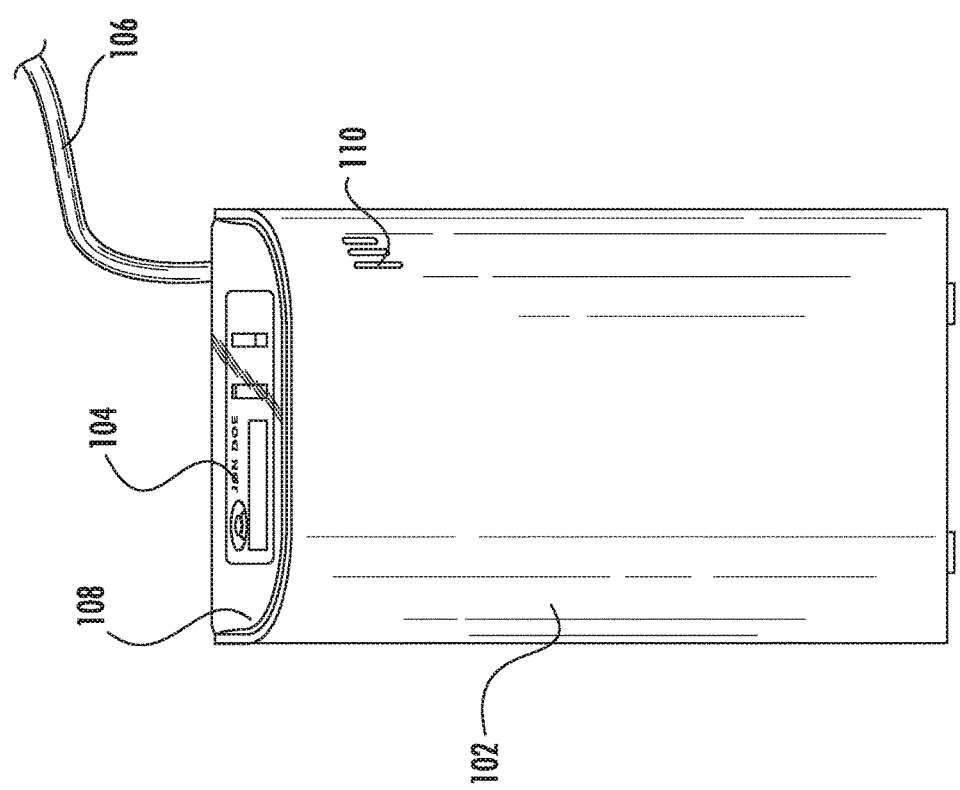
FIG. 2A depicts a front view of a smart catheter device according to an embodiment of the presently disclosed subject matter.

Referring to FIG. 2A, which illustrates a front exterior view of a possible smart catheter 100 of the present disclosure. In some embodiments, the door 102 includes a pattern 110, grooves, or other indicia indicating the direction in which the door 102 opens. This will allow medical professionals to easily determine which way to open the door to increase efficiencies when trying to inspect or exchange components inside the housing of the smart catheter 100.

As shown in FIG. 2B, in some embodiments, the smart catheter 100 of the present disclosure can comprise a clamp and/or bracket 112 on the back of the housing, which can be used to temporarily or permanently fasten or attach the smart catheter 100 to a surface, such as, for example, the side of a hospital bed, a table, or other suitable location. In some embodiments, the smart catheter 100 can be configured such that the flexible tube 106 used to drain the urine can ingress into the smart catheter 100 through the top of the housing. In some embodiments, the flexible tube 106 can ingress into the back of the smart catheter 100 or any other suitable location.

In some embodiments, the smart catheter 100 of the present disclosure can comprise a urinary catheter used to drain urine from the bladder of a patient. In some embodiments, the urinary catheter can comprise, for example and without limitation, a Foley catheter, comprising a flexible tube 106 which a clinician passes through the urethra of a patient and into the patient's bladder to drain urine. In some embodiments, the flexible tube 106 comprises a bladder opening 106-1 at one end and a urine drainage port at an opposing second end (not visible in this view because it is located inside the housing). The bladder opening 106-1 end can be passed through the patient's urethra until the bladder opening 106-1 reaches the patients' bladder. The urine drainage port can be configured to connect or otherwise attach to a collection reservoir, described further herein.

Figure 2C:
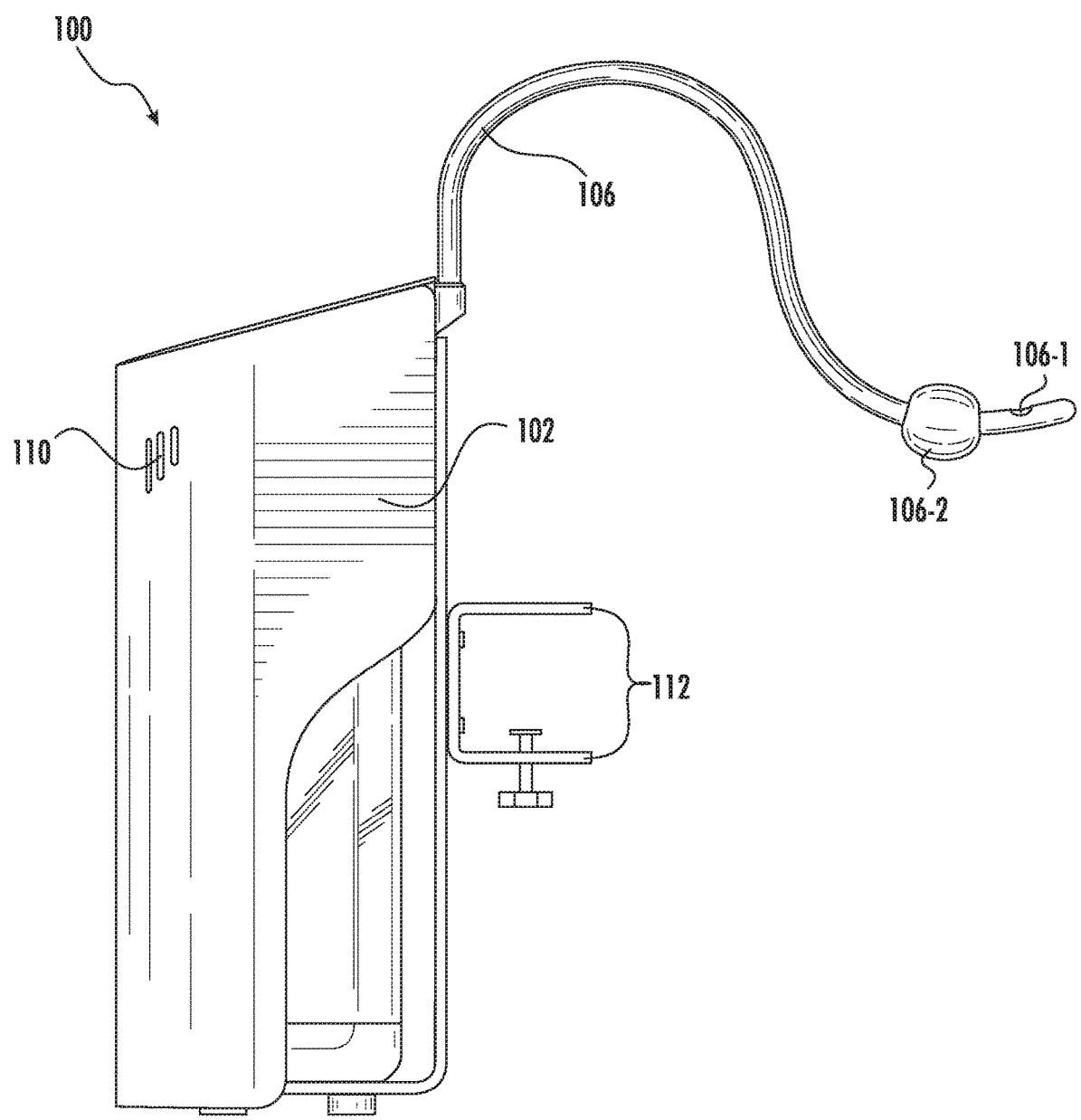

Referring to FIG. 2C, in some embodiments, the flexible tube 106 can also include an inflatable balloon 106-2 at or near the end where the bladder opening 106-1 resides, and a balloon port at the opposing end near where the drainage port resides (i.e., connects to the smart catheter housing). In some aspects, the flexible tube 106 has two separate channels or lumens running down its length. One lumen, open at both ends, connects the bladder opening 106-1 to the urine drainage port and is configured to drain urine from the bladder, through the lumen, out the drainage port and into a collection reservoir, such as, for example and without limitation, a collection bag. The other lumen connects the balloon port 106-2 and the balloon. The balloon 106-2 is inflated with sterile water when it lies inside the bladder to stop the catheter or flexible tube 106 from slipping out.

In some embodiments, the flexible tube 106 can be made of silicone or other suitable material and/or coated natural latex. Coatings can including polytetrafluoroethylene, hydrogel, or a silicon elastomer. In some instances, the different properties of these surface coatings can determine the suitable duration of use, e.g. whether the catheter is suitable for 28-day or 3-month indwelling duration. Additionally, catheters are also changed if soiled, leaking, or if an infection is present.

In some embodiments, the smart catheter 100 can comprise one or more processors (not shown), non-transitory computer readable media, and executable instructions used to operate the various automated functions of the device. In some embodiments, the one or more processors can be configured to operate the display 104, perform various measurements based on sensors described herein, and perform various other functions as described herein.

Figure 3A:
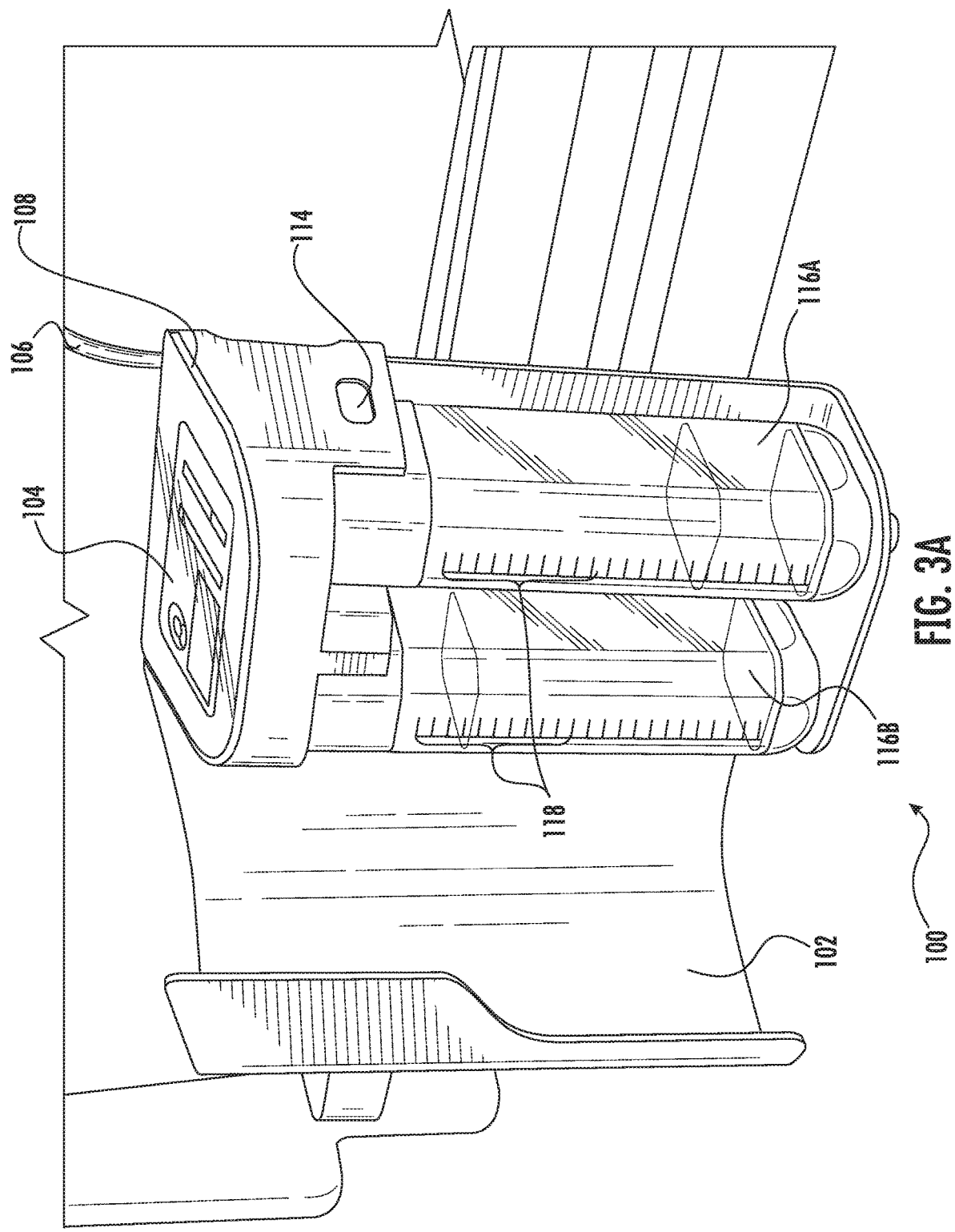
FIG. 3A and FIG. 3B are perspective views of a smart catheter device according to an embodiment of the presently disclosed subject matter with a door of the smart catheter ajar, exposing the internal components of the smart catheter.
Figure 3B:
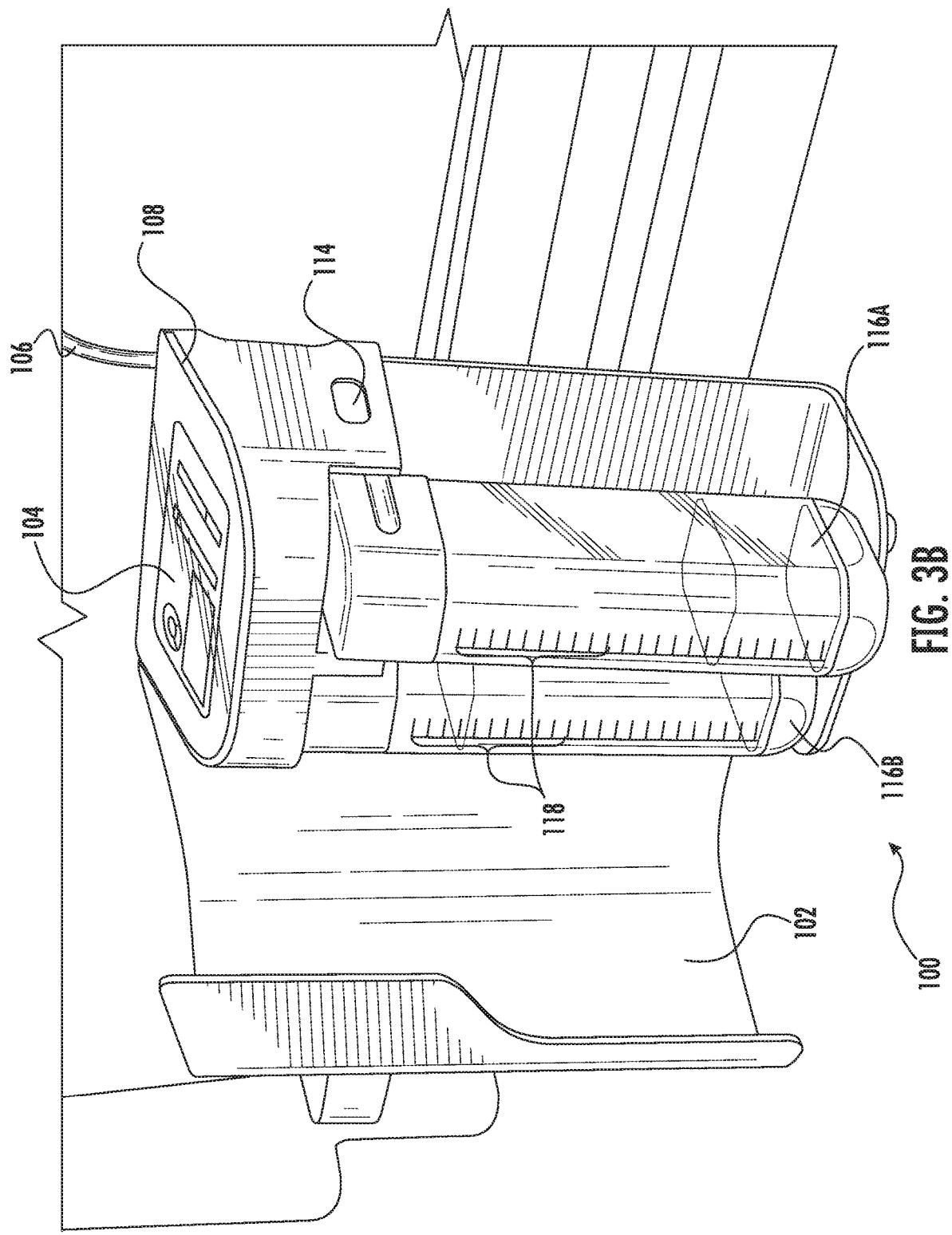

Referring to FIG. 3A and FIG. 3B, in some embodiments, as described above, the housing of the smart catheter 100 can comprise a door 102 configured to open in any suitable direction. For example and without limitation, the door 102 can be hingedly attached to the housing and open up (i.e., like an overhead storage bin in an aircraft) or the door 102 could open out, laterally (i.e., like a typical door). Although the embodiments disclosed in the figures depict a door 102 that is painted, translucent, or non-transparent to obscure the contents of the collection reservoirs 116, in some embodiments, the door 102 can be clear or transparent so that medical staff can easily visually monitor the contents of the collection reservoirs 116. In some embodiments, the housing of the smart catheter 100 can comprise one or more collection reservoirs 116 inside. For example and without limitation, the smart catheter 100 can comprise a first collection reservoir 116A and a second collection reservoir 116B, each configured to collect urine or other fluid as shown in FIG. 3A. As depicted in FIG. 3A, the first collection reservoir 116A and the second collection reservoir 116B can comprise, for example, and without limitation, vials, bags, jars, or any suitable container or reservoir for containing the urine. In some embodiments, each of the first collection reservoir 116A and the second collection reservoir 116B can comprise graduated markings 118 on them to help indicate how full they are for a healthcare worker to manually verify their fill levels. In some embodiments, each of the collection reservoirs 116 can be transparent or non-transparent, For example, if medical staff is required to visually monitor the contents of the collection reservoirs 116, they can be transparent.

As illustrated in FIG. 3B, in some embodiments, the housing of the smart catheter 100 can comprise one or more push buttons 114 to eject one or more of the collection reservoirs. For example and without limitation, in some embodiments, there can be one push button 114 for every collection reservoir or there can be a different push button 114 for each collection reservoir. In some embodiments, the push button 114 and the one or more collection reservoirs 116 can be configured and positioned such that any of the one or more collection reservoirs 116 can be removed using only one hand. For example and without limitation, in some embodiments, the push button 114 can be positioned such that a finger of the hand grasping the body of the collection reservoir 116 can also press the push button 114 to release the collection reservoir 116. As shown in FIG. 3B, one or more of the collection reservoirs, such as for example first collection reservoir 116A, is capable of being removed for inspection, emptying, replacement, or any other suitable purpose.

Referring to FIG. 4A and FIG. 4B in some embodiments, the collection reservoir 116 can comprise a total dissolved solids (TDS) meter 120 or sensor configured for measuring the total dissolved solids in the urine. In some embodiments, the TDS meter 120 is in communication with the one or more processors of the smart catheter 100, wherein the one or more processors is configured to use the TDS meter 120 to capture total dissolved solids measurements of the urine and relay that data or perform various tasks with that data. For example and without limitation, based on outputs from the TDS meter 120, the one or more processors can be configured to transmit statistics about this data to health provider software, or provide outputs on the display 102. This information can then be used to ensure that the health of the patient is being monitored.

Additionally, in some embodiments, one or more color sensors 122, for example and without limitation an RGB sensor can be provided in the collection reservoir 116. In some embodiments, the one or more color sensors 122 can be used to detect and measure a color or shade of the urine. This information can be used to determine the health of the patient, for example, determining whether the patient is dehydrated and needs more fluids or electrolytes, or is bleeding, etc. In some embodiments, the TDS meter 120 and/or the one or more color sensors 122 can be in communication with the one or more processors via a wired or wireless connection and can transmit and receive data and instructions, respectively, regarding their functions and output captures.

FIG. 4B depicts the rear of an example collection reservoir 116, each of the collection reservoirs 116 comprising a quick connect port 124 that allows it to quickly connect to the smart catheter 100. The quick connect port 124 can be configured to allow fluid, including urine, to drain and collect into the collection reservoir 116 from the flexible tube 106 that connects to the top of the housing. Each collection reservoir 116 also comprises, on opposing lateral sides thereof and adjacent to the quick connect port 124, guide rails 126. The guide rails 126 are configured to guide insertion and removal of the collection reservoir 116 into the housing. Although not depicted in the figures, the smart catheter 100 of the present disclosure can comprise an infrastructure inside the housing that connects the flexible tube 106 to the quick connect port 124. In some embodiments, the infrastructure inside the smart catheter 100 can comprise a switch or electric valve which can be configured to select which of the one or more collection reservoirs 116 the flexible tube 106 drains into. In some embodiments, the one or more processors is configured to operate the infrastructure, including the one or more switches or electric valves. In this case, either automatically or manually, the processor is configured to actuate the switch or electric valve to select which collection reservoir 116 is to receive urine. For example and without limitation, once the first collection reservoir 116A gets full or to a certain level, the processor is configured to actuate the switch or valve such that urine or other fluid starts draining into the second collection reservoir 116B. Additionally, if there is a malfunction in a collection reservoir 116, or for some other reason, the smart catheter 100 is configured to allow medical staff to manually select a different collection reservoir 116 and the switch will be actuated to change to the other reservoir. In some embodiments, if the collection reservoir 116 currently being drained into is removed from the device, the smart catheter 100 is configured to automatically move over to any of the other available collection reservoirs 116 that are not themselves already full or malfunctioning.

Additionally, one or more collection reservoirs 116 comprises an electrical connection 128 configured to not only help power the various sensors, meters, and other components within the one or more collection reservoir 116, but also to connect the one or more processors to the various sensors, meters, and other components for performing the actions described herein. For example, and without limitation, each of the TDS meter 120 outputs and the one or more color sensors 122 can measure their respective characteristics of the urine or other fluid in the collection reservoir and then transmit those measurements to the one or more processors via the electrical connection 128. This action can be performed automatically by the sensors themselves (i.e., without any request or query from the processor) or the one or more processors can query the sensors at a constant, periodic, or random time, or, a medical professional could manually request a check of the outputs of the sensors via the display 104 or other computing equipment that is in communication with the smart catheter 100.

In some embodiments, the electrical connection 128 can be used by the smart catheter 100 to communicate with the collection reservoir 116 to determine a fluid level of the collection reservoir 116. In some embodiments, the smart catheter 100 is configured to alarm when at least one of the collection reservoirs 116 is at least half-way full. Furthermore, in some embodiments, the smart catheter 100 is configured to alarm when there is no urine output or not sufficient urine output. These can be set parameters as well. In some embodiments, the alarm could be, for example and without limitation, a signal, message, text message, electronic message, electronic mail, or other appropriate message sent to medical professional mobile devices, tablets, computers, or mobile work stations so that they will be informed of the alarm. Any messages, alarms, or warnings sent via textual or electronic message can include such information as the type of warning, how much of the collection reservoir 116 is full, what its fill level is at, and any other relevant information such as the associated patient, hospital room, or other suitable identifier.

In some other embodiments, the alarm could be, for example a sound made by the smart catheter 116 via a speaker (not shown). In some embodiments, the smart catheter 100 is configured such that it can alarm using an automated voice such as "RESERVOIR FULL", "ALL RESERVOIRS FULL", "RESERVOIR HALF FULL", "RESERVOIR IS X % FULL" (X being any percentage), or any other programmable automated voice sound. In some embodiments, every time urine is deposited into one or more reservoirs, the smart catheter 100 can be configured to alert any of the voice alarms above. In some embodiments, the alarm could be a beep or other sound that occurs once or a few times just to alert the medical professionals working with the patient that the collection reservoir 116 is halfway full. In some embodiments, the smart catheter 100 is configured to trigger an alarm when at least one of the collection reservoirs 116 is almost full and there is only a selectively predetermined volume left, such as 100 ml, before the collection reservoir 116 is completely full. In this particular case, the alarm indicating that the collection reservoir 116 is almost full can be a different sound or have some other indicia (e.g., different tune, different number of beeps, etc.) that indicates that it is a different alarm than the one indicating that the collection reservoir 116 is halfway full. In a similar fashion, if a predetermined minimum threshold of urine has not been collected by the smart catheter 100, as described herein, then an alarm, like those described herein, can be triggered. In some embodiments, if the amount of urine that is collected by the smart catheter 100, as described herein, does not fall within a certain predetermined threshold within a specific amount of time, then an alarm can be triggered, as described herein. In some embodiments, the system will notify of critical values or when set parameters are exceeded. These parameters can be patient specific and thus can be altered or customized by the healthcare officials via the display 104 or via transmissions to the one or more processors on board the smart catheter 100.

In some embodiments, when only a single collection reservoir 116 is inserted in the smart catheter 100, once it is completely full, a similar alarm to those described above will sound and/or appropriate electronic messages described above will be sent. In some embodiments, the smart catheter 100 is configured such that any alarm conveying a sound such as a beep or other alarm sound will continue to alarm until the collection reservoir 116 is exchanged or until the smart catheter 100 is turned off (e.g., if the patient is no longer hooked up to the smart catheter 100). Similarly, if the smart catheter 100 comprises more than one collection reservoir 116, such as the two collection reservoirs 116A and 116B in FIG. 3A and FIG. 3B, the alarm that continuously sounds or alerts will do so when all of the collection reservoirs 116 are full. In some embodiments, these limits described hereinabove can be set and adjusted by medical staff monitoring the smart catheter 100 to address differences in patients and differences in the size of potential collection reservoirs 116. For example and without limitation, the alarms can sound off at any particular set limit and more than three alarms can be set. For example and without limitation, a plurality of alarms can be set to trigger at various fill levels of the collection reservoir 116. The lengths, sounds, chirps, messages, etc. can all be modified or changed to help medical staff to differentiate between which alarm goes to which fill level. All of the alarms, measurements, and other various features of the smart catheter 100 are customizable and adjustable and has sufficient memory and storage to be able to have a plurality of predetermined and preset limits and alarms.

Additionally, in some embodiments, when the smart catheter 100 detects a malfunction with the connection to one or more of the collection reservoirs 116 (or any of the sensors or meters therein), or a malfunction of the display 104, lighting element 108, or any other component of the smart catheter 100, an alarm is configured to be triggered, similar to the alarms described above. In some embodiments, if possible the lighting element 108 can flash a different color if the malfunction has to do with the display 104 or if the malfunction is such that the display 104 cannot be powered or, if the display 104 can be powered, an error message indicative of the malfunction can be displayed on the display 104.

As illustrated in FIG. 4B, in some embodiments, the collection reservoir 116 can comprise a groove to locate and hold the collection reservoir 116. Although they are depicted herein as substantially cylindrical, those having ordinary skill in the art will appreciate that the collection reservoirs 116 and thus, the shape of the smart catheter 100 can be of any suitable shape and size. For example, the collection reservoirs 116 can be flask shaped, cylindrical, bag shaped, bowl shaped, cube shaped, shaped like a rectangular prism, or any suitable three-dimensional shape that can collect and hold fluid. The smart catheter 100 can be modified from the shape illustrated in the present figures to fit any shape described above or any three-dimensional shape.

Figure 5:
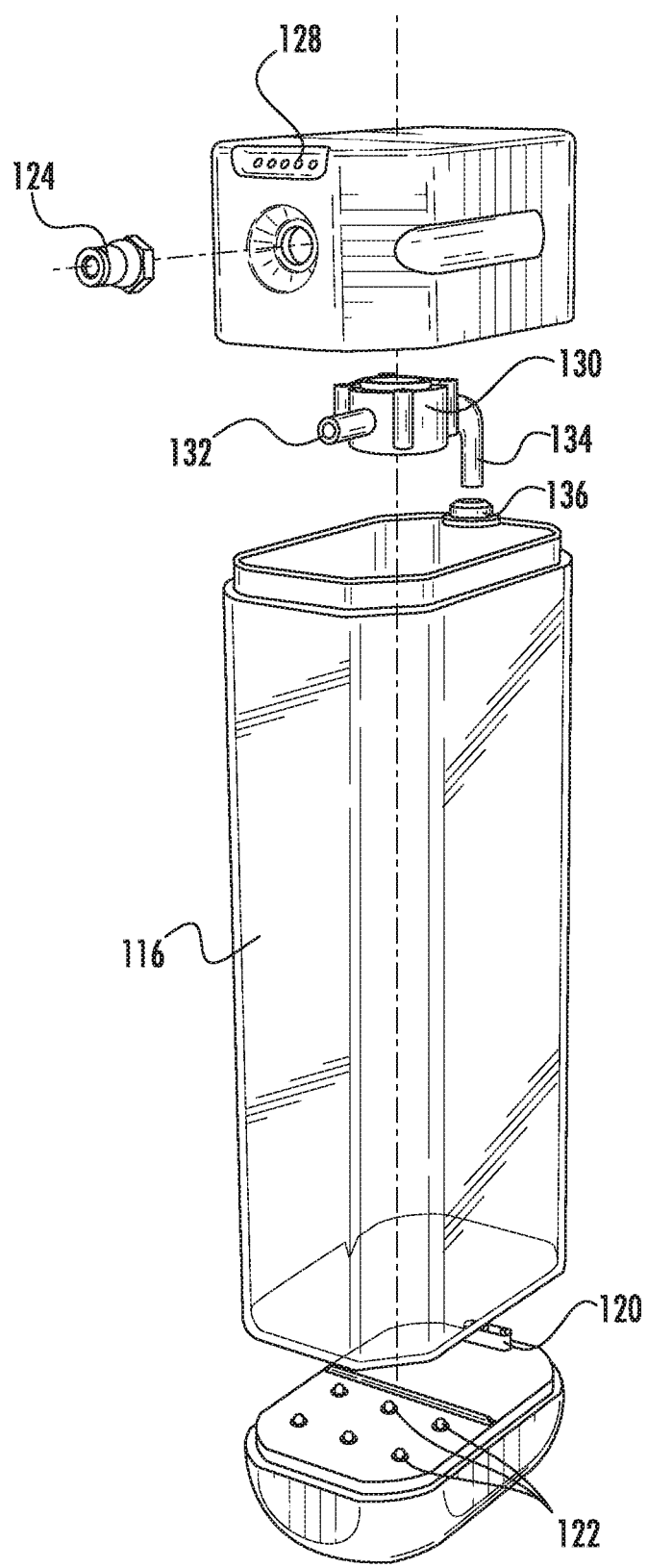
FIG. 5 is an exploded view of a vial or collection reservoir of a smart catheter device according to an embodiment of the presently disclosed subject matter.

FIG. 5 illustrates an exploded view of an example collection reservoir 116 of the present disclosure. In some embodiments, the collection reservoir 116 comprises an inlet port 132 that connects to the infrastructure of the smart catheter 100 via the quick connect port 124. In some embodiments, the inlet port 132 connects to the switch or electronic valve that determines or selects which collection reservoir 116 is meant to receive urine or other fluid at the current time. Once the collection reservoir 116 is properly inserted into the smart catheter 100 and the quick connect port 124 is connected to the infrastructure of the smart catheter 100 and the particular collection reservoir 116 is selected to receive urine, the urine flows through the inlet port 132 to the flow meter 130 which is configured to measure the amount of urine that is collected in the collection reservoir 116. Once the urine flows through the flow meter 130, it flows out the egress port 134 and into the spout 136 of the collection reservoir 116. In some embodiments, the flow meter 130 is configured to measure the volume of urine that flows through it via any suitable means. For example and without limitation, in some embodiments, the flow meter 130 is configured to calculate the flow rate by determining the number of milliliters of fluid per second (or other suitable volume per time period) that flows into the collection reservoir 116 and multiply that by the number of seconds that it detects urine flowing at the given rate. In some embodiments, the flow meter 130 can use more or less accurate measurements of the flow rate to determine a more precise volume of urine in the collection reservoir 116. In some embodiments, the flow meter 130 can be a part of the flexible tube 106 itself and not part of the collection reservoir 116. In other words, the flow meter 130 can be positioned at any suitable location along the flexible tube 106. Furthermore, the flow meter 130 can be integrated into the flexible tube 106 or be a separate piece as shown in FIG. 5. In such an instance where the flow meter 130 is positioned outside of the housing, the flow meter 130 is still in communication with and subject to instructions from the one or more processors via wireless or wired connection.

Figure 6B:
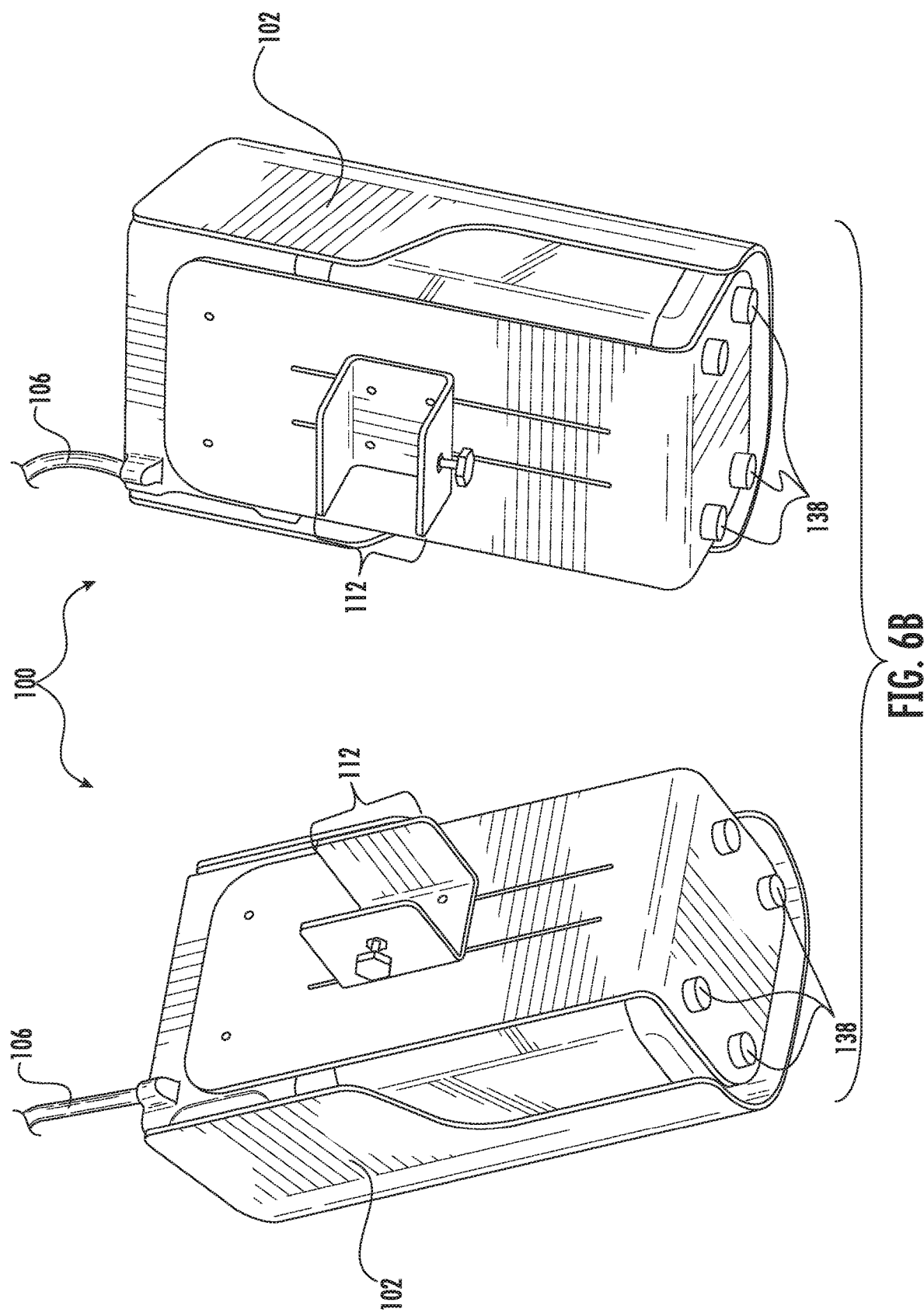
FIG. 6B depicts perspective rear views of a smart catheter device according to an embodiment of the presently disclosed subject matter.

Referring to FIG. 6A and FIG. 6B, in some embodiments, the smart catheter 100 can comprise one or more rubber feet 138 on the bottom of the device such that if the device were positioned on a surface, any sliding of the device would be minimized. Additionally, as illustrated in FIG. 6B, in some embodiments, the clamp and/or bracket 112 on the back can be rotated such that the opening of the clamp and/or bracket 112 is either parallel to the length of the housing of the smart catheter 100 or perpendicular to the length of the housing of the smart catheter 100. Those having ordinary skill in the art will appreciate that the clamp and/or bracket 112 can be adjusted up or down along a track on the back of the smart catheter 100 as well. Moreover, in some embodiments, the clamp and/or bracket 112 is rotatable in place and doesn't need to be removed in order to rotate it to be parallel with or perpendicular with respect to the smart catheter 100. Furthermore, in some embodiments, the clamp and/or bracket 112 can be configured to mount the smart catheter 100 to a standard hospital bed frame, transport poles, or any other suitable location. For example and without limitation, the clamp or bracket 112 can be configured to attach the smart catheter 100 housing or enclosure to a bed or other frame, pole, or other suitable attachment point with dimensions of ½", 1", 1½", 2", 2½", etc.

Figure 7:
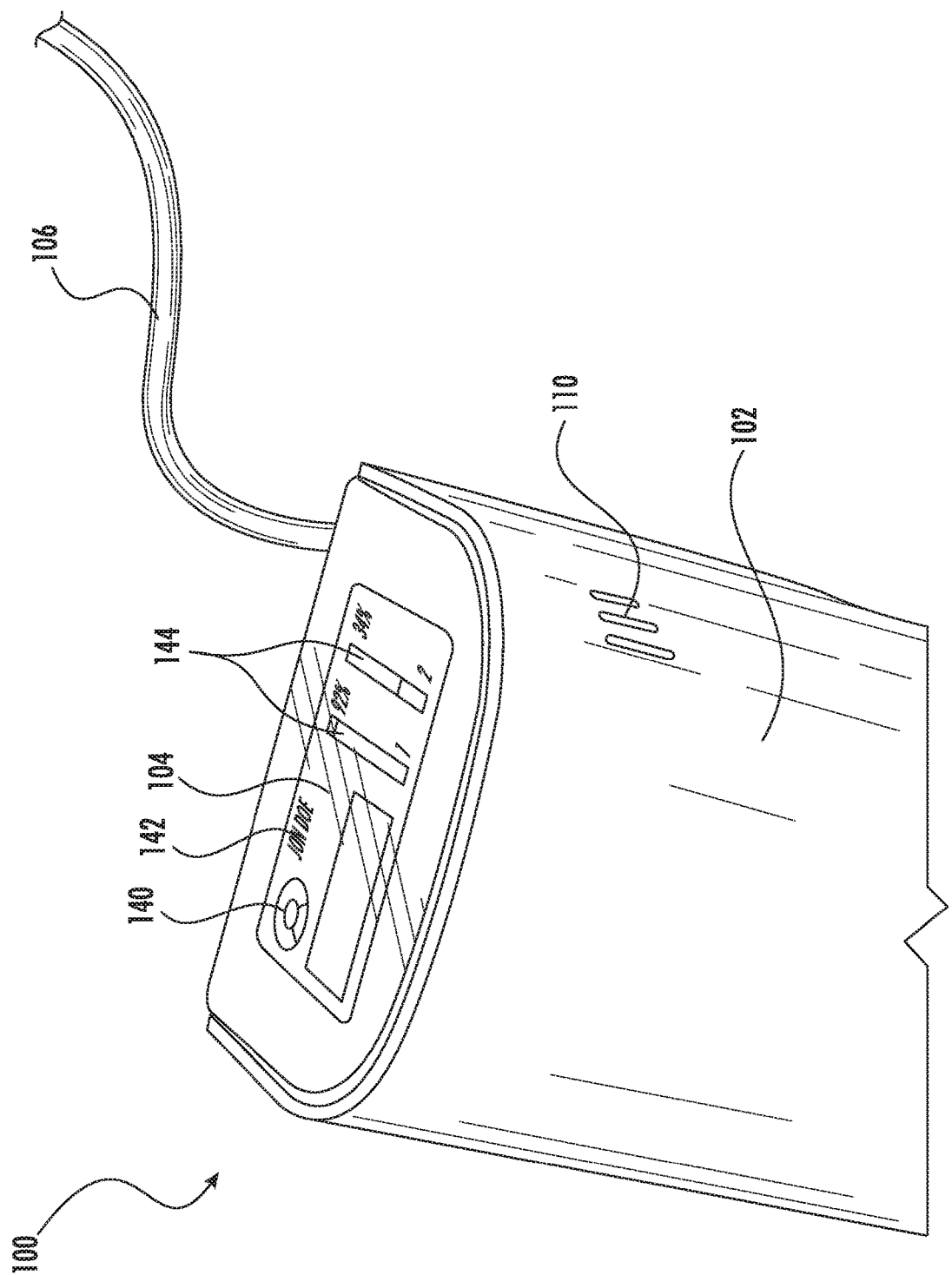
FIG. 7 is a close-up perspective top view of a smart catheter device according to an embodiment of the presently disclosed subject matter.

Referring to FIG. 7, in some embodiments, the smart catheter 100 of the present disclosure is configured to present various pieces of information on the display 104. For example and without limitation, the display 104 can be configured to show information identifying the patient for which the particular smart catheter 100 is being used for. Such identifying information could be a picture 140 or avatar of the patient or the patient's name 142, or patient identification number. In addition, in some embodiments, fluid levels 144 or capacities of each collection reservoir 116 can be displayed. In some embodiments, the one or more processors situated within the housing of the smart catheter 100 can control what and when items are displayed. In some embodiments, the alarms described herein can coincide with various indicators flashing on the display 104 to help alert healthcare workers of the issue. Additionally, in some embodiments, the display can flash the fluid level 144 indicator of one more of the collection reservoirs 116 when they have reached certain thresholds. In this way, medical staff can easily determine which collection reservoir 116 is full before even opening up the door 102. In some embodiments, the display 104 can also show pertinent information about the urine, such as for example, any dissolved solids statistics or other information. In some embodiments, the display 104 is configured to light up to match the color of the urine. In some further embodiments, the display 104 has the ability to have sensor motion to turn the light on from dim to bright.

Those having ordinary skill in the art will appreciate that the display 104 can be configured to display any appropriate information that relates to the patient, medical workers, the status of the smart catheter 100 or any of its parts, etc. To allow a medical professional who is operating and monitoring the smart catheter 100 to have easier control over the device, the display 104 can be a touchscreen display that has multiple different pages, folders, and buttons that can be displayed, changed, altered, customized, etc. Additionally, in some embodiments, the one or more processors can be in communication with one or more external devices. In some embodiments, the external devices comprises servers or other computers hosting the patient's medical records and/or medical chart. In such an embodiment, the one or more processors can be configured to automatically measure the amount or volume of urine according to predetermined sets of time (e.g., continuously, periodically, randomly, every 30 minutes or Q one hour, etc.) in one or more of the collection reservoirs 116 and transmit a volume of urine in total or in each of the collection reservoirs 116. Additionally, information about the urine gleaned from the various sensors can also be recorded and sent to the medical records and/or medical chart for updating.

Moreover, in some embodiments, the external device comprises a tablet, computer, mobile device, phone, smart watch, audio device, handheld documentation device or display device. In some embodiments such a catheter as provided herein further comprises a power source, a computer, memory, a receiver or transmitter, an accelerometer, a speaker, microphone, or a tactile signal device, wherein the power source, computer, memory, receiver or transmitter, accelerometer, speaker or tactile signal device are interconnected with one another. In some embodiments such a catheter as provided herein further comprises a computer program product comprising computer executable instructions embodied in a computer readable medium for performing steps comprising receiving an electrical signal from a measuring apparatus, processing the electrical signal to calculate data pertaining to a measured volume, and relaying the data to the electronic display, speaker, tactile signal device or external device. In some embodiments, a wireless receiver is configured to receive data wirelessly and transfer it to a computer, wherein the computer is configured to process the data and transmit it to the display, speaker or tactile signal device.

The functions and subject matter described herein, especially with respect to the one or more processors described herein, can in some embodiments be implemented using a computer program product comprising computer executable instructions embodied in a computer readable medium. Such computer readable medium can be stored in memory and implemented by computer. Exemplary computer readable media suitable for implementing the subject matter described herein include disk memory devices, chip memory devices, application specific integrated circuits, programmable logic devices, and downloadable electrical signals. In addition, a computer program product that implements the subject matter described herein may be located on a single device or computing platform or may be distributed across multiple devices or computing platforms.

All of the above measurements and transmissions can be done in real time or after the fact (i.e., as soon as urine flows and stops flowing into the collection reservoir 116, the smart catheter 100 can transmit the volume data and urine characteristics data to the medical records server). In some embodiments, the smart catheter 100 can comprise a transmitter, transmission device, or transceiver for making a wired or wireless connection to the medical records and/or medical chart server/computer. Moreover, in some embodiments, the smart catheter 100 comprises a receiver, such as, for example and without limitation, a wireless or wired receiver configured to receive data from an external device. Using the one or more processors and transmitter and/or receiver, any component of the smart catheter 100 can receive or transmit data to/from any suitable external or internal device (i.e., such as the medical records or medical chart server, mobile phones, tablets, medical equipment, etc.). A wireless receiver and/or transmitter can be configured to wirelessly receive and/or transmit data and information via wireless signal. By way of example and not limitation, such wireless forms of communication can comprise Wi-Fi and Bluetooth. As described herein, with integrated wireless communication capabilities, catheters can exchange information and/or data, i.e. receive and/or transmit, with another device, such as but not limited to a tablet, computer, phone, smart watch, audio device or display device.

In some embodiments, the smart catheter 100 can be powered by a wired power cable connected to an electrical outlet. In further embodiments, the smart catheter 100 can be powered by a battery or other suitable power source. In either embodiments, the smart catheter 100 can be configured to trigger and sound an alarm as described herein when either the power connection is inadequate, or there is a malfunction with the power connector or the battery or other power source. Additionally, in some embodiments, the smart catheter 100 can be operable using speech recognition. In support of this feature, some embodiments of the smart catheter 100 of the present disclosure comprise speakers and an audio input device, such as a microphone, that allow a user to speak to the smart catheter 100 to issue commands or requests. Moreover, in such an embodiment, the one or more processors of the smart catheter 100 can be configured to operate an artificial intelligence program that is configured to receive spoken commands and respond with additional audio feedback or perform tasks in connection with the commands. In this way, any of the parameters, actions, services, or performances that can be performed automatically, or manually be a person touching the smart catheter 100 can also be performed via voice command using speech recognition.

Smart Chest Tube

In some embodiments of the present disclosure, the smart catheter 100 can be retrofitted to act as a smart chest tube, instead. Provided herein are smart chest tubes, also referred to herein as precise chest tubes, KG chest tubes, chest tubes and/or electronic chest tubes. A chest tube is a flexible plastic tube that is inserted through the chest wall and into the pleural space or mediastinum. It is used to remove air, fluid, pleural effusion, blood, chyle, or pus from the intrathoracic space. It is also known as a Bülau drain or an intercostal catheter.

In some cases, pressure around the lungs is lower than atmospheric pressure outside the body. The aims for an adequate chest drainage system to be fulfilled are: (i) remove fluid and air as promptly as possible; (ii) prevent drained air and fluid from returning to the pleural space, restore negative pressure in the pleural space to re-expand the lung. Thus, in some embodiments, a drainage device can: (i) allow air and fluid to leave the chest; (ii) contain a one-way valve to prevent air and fluid from returning to the chest; (iii) comprise a design so that the device is below the level of the chest tube for gravity drainage. An underwater seal chest drainage system can be used to restore proper air pressure to the lungs, re-inflate a collapsed lung as well as remove blood and other fluids. The system is a two-chambered or three-chambered plastic unit with vertical columns bringing measurements marked in milliliters. The thoracic drainage devices cover a wide range and have evolved considerably since their introduction. The basic design principle of these systems has been the avoidance of air entrance in the pleural cavity during the various phases of the respiratory cycle and continuous drainage of air and fluid from the pleural cavity. The water seal chamber, which is connected in series to the collection chamber, allows air to pass down through a straw or narrow channel and bubble out through the bottom of the water seal. Since air must not return to the patient, a water seal is considered one of the safest and cost-effective means for protecting the patient, in addition to being a very useful diagnostic tool. The water seal column is calibrated and acts as a water manometer for measuring intrathoracic pressure.

In a traditional water seal operating system, fluids drain from the patient directly into a large collection chamber via a tube, e.g. a six-foot ⅜-inch tube. As drainage fluids collect in this chamber, a nurse or other practitioner can record the amount of fluid that collects on a specified schedule. Unfortunately, the measuring and recording of the drainage fluid is still done manually. What is needed is an automated and accurate measurement and recording device.

Figure 8:
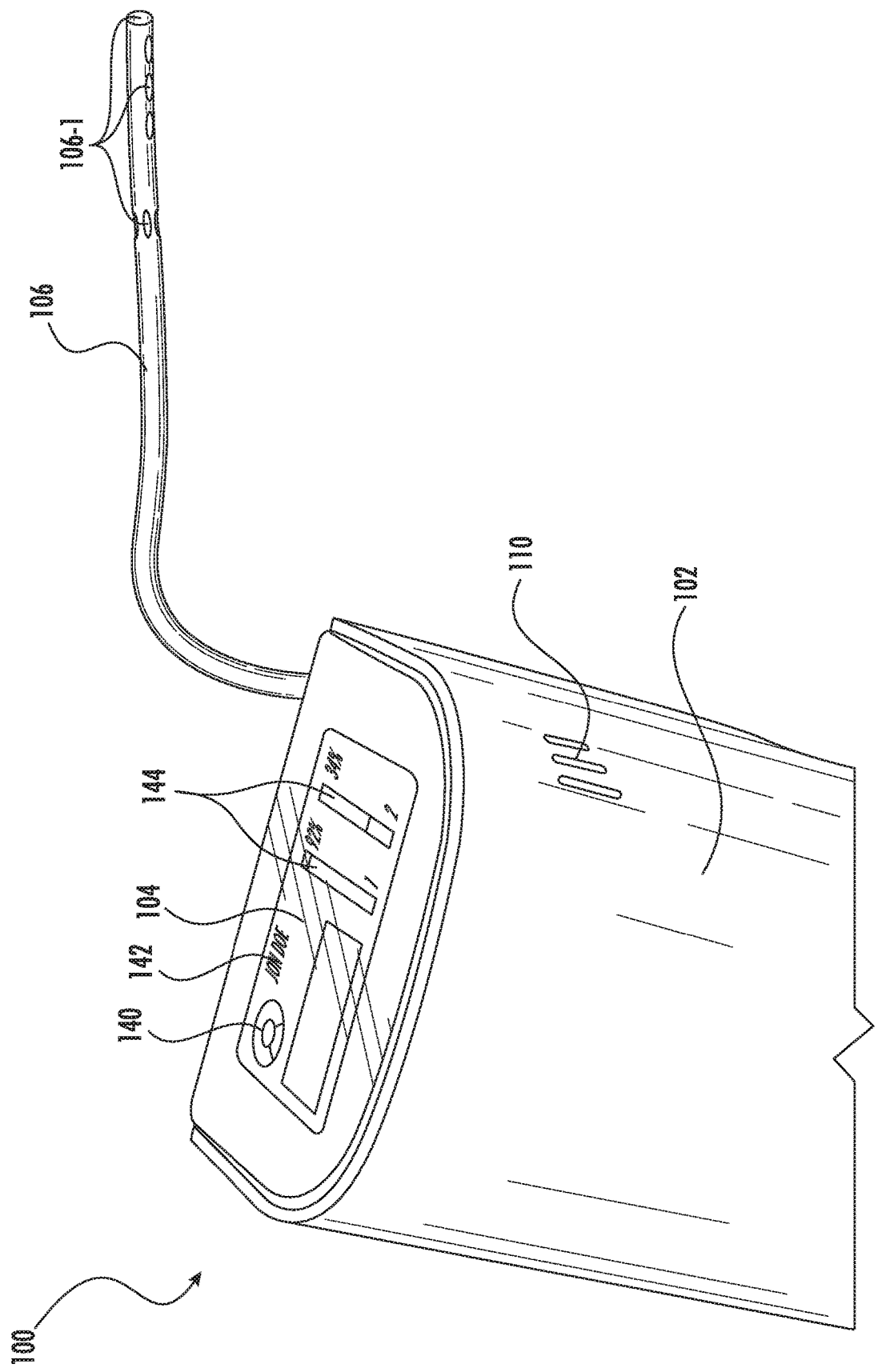
FIG. 8 is a close-up perspective to view of a smart chest tube device and illustrates the details of the flexible tube according to an embodiment of the presently disclosed subject matter.

Referring to FIG. 8, in some embodiments, the smart chest tube of the present disclosure can look virtually identical to the smart catheter 100 of FIG. 1-FIG. 7 and have virtually all the same components. However, for a smart chest tube, additional components are required, as those having ordinary skill in the art will fully appreciate. These components are well known in the art. Specifically, the measuring devices, sensors, and other pieces of equipment described hereinabove can be altered to be able to receive and measure air, fluid, pleural effusion, blood, chyle, or pus flowing from the intrathoracic space through the chest tube. The flexible tube 106 can be replaced or altered to operate as a chest tube, wherein the flexible tube 106 comprises one or more openings at one end 106-1, and a drainage port at the opposing end. In some embodiments, the one or more openings 106-1 can be located at the end face of the flexible tube 106, or they can be axially aligned, meaning they run down the length of the flexible tube 106, starting near the end. In some other embodiments, the one or more openings 106-1 can be circumferentially aligned, meaning around the circumference of the flexible tube 106.

In some embodiments, the flow meter 130 of FIG. 5 is configured to measure an amount of air, fluid, pleural effusion, blood, chyle, and/or pus flowing therethrough, instead of urine. The flow meter 130 can be adapted to properly measure almost any fluid flowing therethrough.

The measured volume of air, fluid, pleural effusion, blood, chyle, or pus determined by the flow meter 130 can be transmitted as data to an external device, e.g. a computer or receiver. As described herein, the smart chest tube device can in some embodiments comprise a transmitter or transmission device to wirelessly transmit the data to an external device. The smart chest tube can in some embodiments also comprise a receiver configured to receive data from an external device.

In some embodiments, when the device is retrofitted as a smart chest tube, the device is configured to measure and calculate the volume of air, fluid, pleural effusion, blood, chyle, or pus produced by a patient and activate an alarm if such volume output exceeds or does not meet a set or predetermined threshold, or as described above, if the collection reservoirs 116 are full, about to be full, or if there is a malfunction. All of the features and aspects described above with respect to the smart catheter 100 can be retrofitted and slightly altered to account for any differences in the operations of a urinary catheter versus a chest tube. For example, tubes and ports sizes can be increased and materials can be altered to make it more available for puss and chyle storage.

Additionally, for the smart chest tube application, the smart catheter 100 as described herein can be retrofitted with a suction control chamber to help suction the fluid being drained from the chest cavity of the patient.

The present subject matter can be embodied in other forms without departure from the spirit and essential characteristics thereof. The embodiments described therefore are to be considered in all respects as illustrative and not restrictive. Although the present subject matter has been described in terms of certain specific embodiments, other embodiments that are apparent to those of ordinary skill in the art are also within the scope of the present subject matter.

What is claimed is:

1. A smart catheter comprising:
an enclosure;
a flexible tube comprising:
   an opening at a first end of the flexible tube;
   a drainage port at a second end of the flexible tube, wherein the second end is opposite the first end;
   an inflatable balloon at the first end, proximate to the opening; and
   a balloon port at the second end, proximate to the drainage port; and
two or more collection reservoirs removably contained within the enclosure and configured to receive a flow of a fluid therein from the flexible tube, each of the two or more collection reservoirs comprising:
   an upper portion comprising:
      an inlet port on a rear face of the upper portion and configured to receive the flow of the fluid from the flexible tube, wherein the inlet port is a quick connect port;
      an electrical connection on the rear face of the upper portion, the electrical connection being configured to provide power to components of a same one of the two or more collection reservoirs; and
      guide channels, one on each opposing lateral face of the upper portion, wherein the guide channels are coincident with and extend away from the rear face, and are configured such that the collection reservoir slides into the enclosure to engage the inlet port with the drainage port of the flexible tube;
   a flow meter contained within the upper portion of the collection reservoir and attached between the inlet port and the collection reservoir, wherein the flow meter is configured to measure a flow rate of the fluid flowing through the flow meter; and
   a lower portion attached to the upper portion and comprising a spout;
wherein, after the fluid flows through the flow meter, the fluid flows out of an egress port of the flow meter and into the spout;
wherein, when either of the two or more collection reservoirs is installed within the enclosure, the inlet port and the electrical connection thereof faces a rear of the enclosure; and
wherein the drainage port is fluidically connected to the one or more collection reservoirs within the enclosure.

2. The smart catheter of claim 1, wherein the fluid is urine and the smart catheter is configured to drain the urine from a bladder of a patient.

3. The smart catheter of claim 2, wherein the flow meter is configured to measure an amount of the urine deposited into whichever of the two or more collection reservoirs the flow meter is provided.

4. The smart catheter of claim 1, wherein the flexible tube comprises two separated channels or lumens running along a length of the flexible tube, wherein a first lumen, open at both ends, connects the opening at the first end to the drainage port at the second end, wherein the second lumen connects the inflatable balloon to the balloon port.

5. The smart catheter of claim 1, wherein:
the enclosure comprises:
   a transparent door; or
   a non-transparent door; and
each of the one or more collection reservoirs is:
   transparent; or
   non-transparent.

6. The smart catheter of claim 1, wherein:
the smart catheter comprises one or more processors, one or more transmitters, and one or more receivers; and
the one or more processors is configured to transmit and receive data, via the one or more transmitters or one or more receivers, to or from one or more computing device in communication with the smart catheter.

7. The smart catheter of claim 6, wherein:
the transmitted data comprises urine flow data;
at least one of the one or more computing devices is configured to store and monitor the urine flow data;
the one or more processors and the at least one computing device is configured to monitor the flow rate of the urine deposited into either of the two or more collection reservoirs of the smart catheter; and
the one or more processors is configured to transmit a warning signal or trigger an alarm when at least one of the two or more collection reservoirs of the smart catheter reaches one or more thresholds.

8. The smart catheter of claim 6, wherein the one or more processors is configured to transmit a warning signal or trigger an alarm when there is a malfunction of the smart catheter.

9. The smart catheter of claim 1, wherein the enclosure comprises a display screen configured to display fill levels of one or both of the two or more collection reservoirs of the smart catheter.

10. The smart catheter of claim 1, wherein at least one of the two or more collection reservoirs comprises a total dissolved solids meter and/or a color sensor configured to detect and measure a color or shade of the fluid.

11. The smart catheter of claim 1, wherein at least one of the two or more collection reservoirs comprises a quick connect port to connect the at least one of the two or more collection reservoirs to the flexible tube.

12. The smart catheter of claim 1, wherein:
the two or more collection reservoirs comprises at least a first collection reservoir and a second collection reservoir; and
when the first collection reservoir is removed from the smart catheter, the smart catheter is configured to automatically select the second collection reservoir and start draining the fluid into the second collection reservoir.

13. A smart catheter system comprising:
the smart catheter of claim 1; and
an external device, wherein the external device comprises a tablet, computer, phone, smart watch, audio device or display device.

14. The smart catheter of claim 1, wherein each of the two or more collection reservoirs comprises an electrical connection configured to provide power to various components in a respective one of the two or more collection reservoirs and to connect the one or more processors to components in the respective one of the two or more collection reservoirs.

15. The smart catheter system of claim 13, comprising:
a power source, one or more processors, memory, a receiver or transmitter, a display, an accelerometer, a speaker and/or a tactile signal device,
wherein the smart catheter, power source, one or more processors, memory, receiver or transmitter, display, accelerometer, speaker, or tactile signal device are interconnected with one another.

16. The smart catheter system of claim 15, wherein the display is configured to display information about:
   the patient and/or the smart catheter;
   the patient as well as information regarding the patient's urine; and/or
   a capacity of each of the two or more collection reservoirs or a warning or error message.

17. The smart catheter system of claim 13, comprising a computer program product comprising computer executable instructions embodied in a computer readable medium for performing steps comprising:
   receiving an electrical signal from the measuring device;
   processing the electrical signal to calculate data pertaining to a measured volume of the fluid; and
   relaying the data to the electronic display, speaker, tactile signal device, or external device.

18. The smart catheter system of claim 13, wherein:
   the fluid is urine or another bodily fluid; and
   the smart catheter system is configured to measure and calculate a volume of the urine or the other body fluid produced by a patient every 30 minutes or one hour, wherein the calculated volume is processed by a computer and entered into an electronic charting system.

19. The smart catheter system of claim 13, wherein:
   the fluid is urine or another bodily fluid; and
   the smart catheter system is configured to measure and calculate a volume of the urine or the other body fluid produced by a patient and activate an alarm when the volume of the urine and/or of the other body fluid is above and/or below a predetermined threshold.

* * * * *